United States Patent
Ikudome et al.

(10) Patent No.: US 6,627,773 B1
(45) Date of Patent: Sep. 30, 2003

(54) PROCESS FOR PRODUCING 2-HYDROXY-4-METHYL-THIOBUTANOIC ACID

(75) Inventors: Kenji Ikudome, Niihama (JP); Tetsuya Shiozaki, Saijo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/869,412

(22) PCT Filed: Feb. 1, 2000

(86) PCT No.: PCT/JP00/00542
§ 371 (c)(1),
(2), (4) Date: Jun. 28, 2001

(87) PCT Pub. No.: WO00/46190
PCT Pub. Date: Aug. 10, 2000

(30) Foreign Application Priority Data

Oct. 21, 1999 (JP) ............................................. 11-299475
Feb. 3, 1999 (JP) ............................................. 11-026491

(51) Int. Cl.⁷ ........................ C07C 381/00; C07C 51/16
(52) U.S. Cl. ...................................... 562/581; 562/526
(58) Field of Search ................................ 562/581, 526

(56) References Cited

U.S. PATENT DOCUMENTS

| | | | |
|---|---|---|---|
| 2,745,745 A | * 5/1956 | Blake et al. ................. | 514/557 |
| 3,175,000 A | 3/1965 | Gielkens et al. | |
| 4,353,924 A | * 10/1982 | Baker et al. ................. | 514/557 |
| 4,579,962 A | * 4/1986 | Takano ........................ | 556/131 |
| 4,912,257 A | * 3/1990 | Hernandez et al. ......... | 562/581 |
| 5,386,056 A | * 1/1995 | Matsuoka ................... | 562/526 |
| 5,973,198 A | * 10/1999 | Shiozaki et al. ............ | 562/526 |

FOREIGN PATENT DOCUMENTS

| EP | 0863135 | 9/1998 |
|---|---|---|
| EP | 0863135 A2 * | 9/1998 |

* cited by examiner

Primary Examiner—Alan L. Rotman
Assistant Examiner—Taylor V. Oh
(74) Attorney, Agent, or Firm—Stevens, Davis, Miller & Mosher, L.L.P.

(57) ABSTRACT

A process for producing 2-hydroxy-4-methylthiobutanoic acid is provided wherein 2-hydroxy-4-methylthiobutyronitrile is converted to 2-hydroxy-4-methylthiobutanamide by using sulfuric acid, then adding an aqueous solution containing ammonium bisulfate and ammonium sulfate to the reaction liquid to obtain an oil layer containing 2-hydroxy-4-methylthiobutanoic acid and an aqueous layer containing ammonium bisulfate and ammonium sulfate, then a part of the ammonium salts is separated from the aqueous layer, and the aqueous layer containing ammonium bisulfate and ammonium sulfate thus obtained is recycled as the aqueous solution containing ammonium bisulfate and ammonium sulfate described above.

According to the present invention, 2-hydroxy-4-methylthiobutanoic acid of high quality can be obtained without requiring organic solvents and with a greatly reduced amount of waste water.

14 Claims, 1 Drawing Sheet

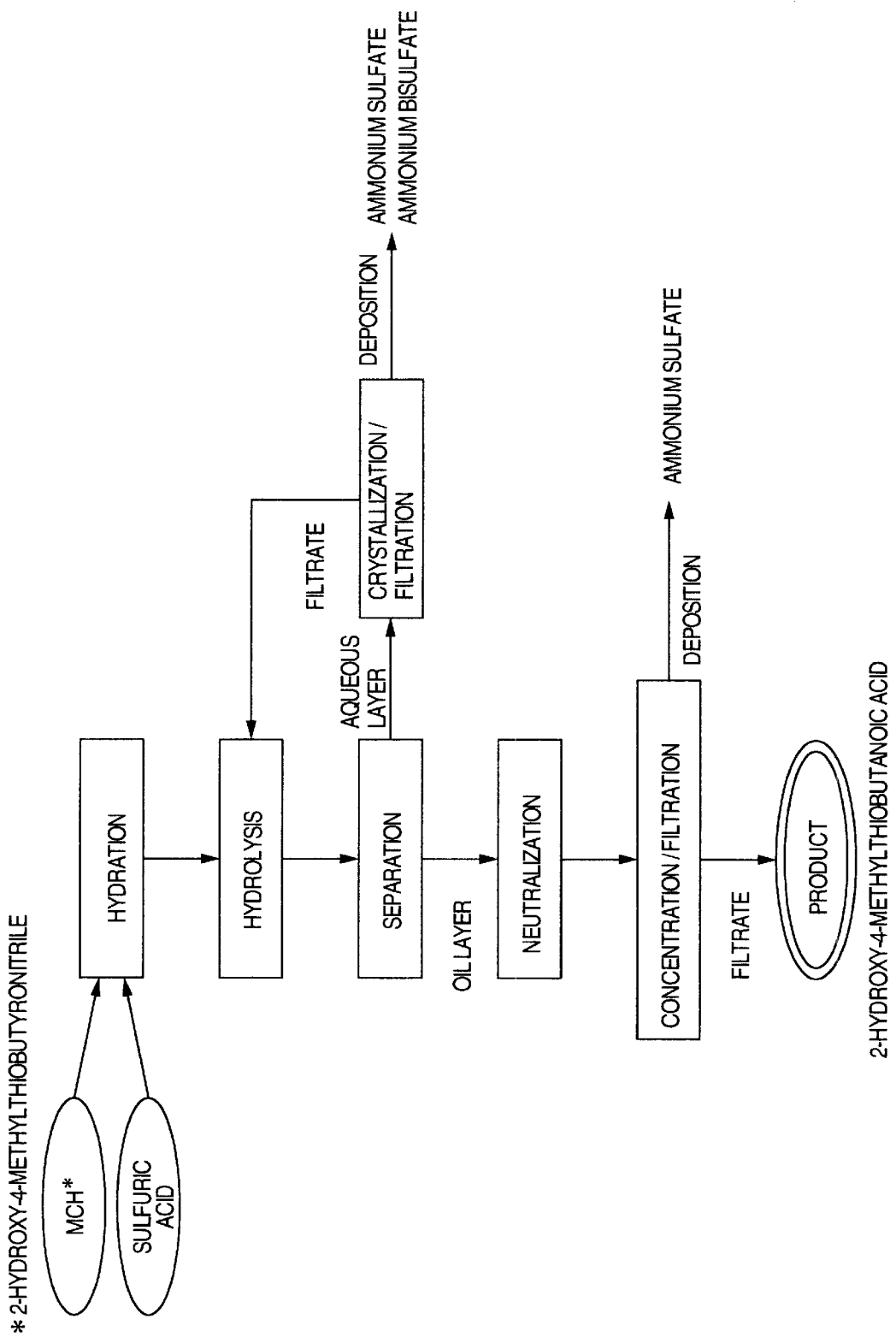

PROCESS FOR PRODUCING 2-HYDROXY-4-METHYL-THIOBUTANOIC ACID

TECHNICAL FIELD PERTINENT TO THE INVENTION

The present invention relates to a process for producing 2-hydroxy-4-methylthiobutanoic acid, which is useful as a feed additive and for other uses. In more particular, it relates to a process for producing 2-hydroxy-4-methylthiobutanoic acid which permits a reduction of the amount of waste water produced and makes the use of organic solvents unnecessary by recycling and reusing the aqueous solution containing ammonium bisulfate and ammonium sulfate formed after the reaction of the process.

BACKGROUND OF THE INVENTION

A generally known process for producing 2-hydroxy-4-methylthiobutanoic acid comprises subjecting 2-hydroxy-4-methylthiobutyronitrile to hydration and successive hydrolysis by using sulfuric acid. A typical method used for separating the intended 2-hydroxy-4-methylthiobutanoic acid from the reaction liquid resulting from the above-mentioned reaction includes a method comprising the use of an organic solvent, typically represented by methyl isobutyl ketone, as an extraction solvent (see JP-B-7-97970).

However, the method which uses an organic solvent cannot be regarded as the best one, because it requires the cost for solvent and increased investment for equipment necessary for recovering the solvent, increases load on environment, and moreover much care must be taken to avoid the contamination of the final product by the solvent.

Another proposed method is a method comprising neutralizing the ammonium bisulfate contained in the reaction liquid with ammonia to form ammonium sulfate and then separating 2-hydroxy-4-methylthiobutanoic acid from the resulting reaction system by salting-out (see U.S. Pat. No. 4,912,257). This method, however, is not so advantageous, because it consumes large ammounts of sulfuric acid and ammonia.

To say the least, the above-mentioned methods are not preferable from the viewpoint of environmental friendliness, because they use a large amount of sulfuric acid and produce a large amount of ammonium sulfate as a by-product.

On the other hand, a method has been proposed which comprises separating ammonium sulfate from the aqueous layer obtained by layer separation after the reaction thereby to recover an aqueous ammonium bisulfate solution, and recycling the aqueous solution to the reaction system (see Japanese Patent Application No. 9-248592). This method is preferable in point of permitting reduction of the amount of sulfuric acid used, reduction of the amount of by-produced ammonium sulfate and reduction of waste water load. However, it is difficult to reduce environmental load markedly by this method, because it uses an alcohol, such as methanol, for separating ammonium sulfate and ammonium bisulfate from each other.

SUMMARY AND OBJECTS OF THE INVENTION

The present inventors have made extensive study with the object of providing a process for producing 2-hydroxy-4-methylthiobutanoic acid which does not use organic solvents, such as methanol and methyl isobutyl ketone, and moreover permits reduction of the amount of ammonium sulfate by-produced and of waste water load, which is the advantage of the technique disclosed in Japanese Patent Application No. 9-248592. As the result, it has been found that, in the process for producing 2-hydroxy-4-methylthiobutanoic acid by using sulfuric acid, (1) addition of a mixed aqueous solution of ammonium bisulfate and ammonium sulfate to the hydrolysis reaction system promotes the hydrolysis, (2) a layer separation phenomenon takes place rapidly after the above-mentioned reaction, (3) the oil layer obtained by the layer separation can provide, through such operations as neutralization and filtration, a 2-hydroxy-4-methylthiobutanoic acid product equivalent in quality to prior products, and (4) the aqueous layer obtained by the layer separation can be recycled, through succeeding such operations as crystallization and filtration, as a mixed aqueous solution used in (1) above. The present invention has been accomplished on the basis of the above findings.

Thus, the present invention provides a process for producing 2-hydroxy-4-methylthiobutanoic acid comprising the steps of:

(A) contacting an aqueous solution of 2-hydroxy-4-methylthiobutyronitrile with sulfuric acid to obtain an aqueous solution containing 2-hydroxy-4-methylthiobutanoamide, (B) adding an aqueous solution containing ammonium bisulfate and ammonium sulfate to the solution obtained by step (A), to obtain an aqueous solution containing 2-hydroxy-4-methylthiobutanoic acid, (C) allowing the aqueous solution obtained by step (B) to separate into two layers of an oil layer and an aqueous layer, and then separating the oil layer and the aqueous layer from each other, (D) adding ammonia to the oil layer separated in step (C) to neutralize at least part of the ammonium bisulfate in the oil layer to form crystals of ammonium sulfate or crystals of sulfates including ammonium sulfate and ammonium bisulfate, and thereafter removing the crystals from the neutralized oil layer to obtain 2-hydroxy-4-methylthiobutanoic acid, (E) cooling and/or concentrating the aqueous layer separated in step (C) to obtain an aqueous solution containing ammonium bisulfate and ammonium sulfate as well as crystals of sulfates including ammonium sulfate and ammonium bisulfate, and (F) recycling all or part of the aqueous solution containing ammonium bisulfate and ammonium sulfate obtained by step (E), to step (B) as the aqueous solution containing ammonium bisulfate and ammonium sulfate.

BRIEF DESCRIPTION OF DRAWING

FIG. 1 is a flow sheet showing one embodiment of the process of the present invention as a block diagram.

DETAILED DESCRIPTION OF THE INVENTION

In the process for producing 2-hydroxy-4-methylthiobutanoic acid according to the present invention, there are conducted step (A) of contacting an aqueous solution of 2-hydroxy-4-methylthiobutyronitrile with sulfuric acid to obtain an aqueous solution containing 2-hydroxy-4-methylthiobutanamide and step (B) of adding to the solution thus obtained an aqueous solution containing ammonium bisulfate and ammonium sulfate to obtain an aqueous solution containing 2-hydroxy-4-methylthiobutanoic acid. According to the present invention, in the aqueous solution obtained in step (B), a layer separation phenomenon due to salting-out takes place rapidly.

In the present invention, following step (B), there is conducted step (C) of allowing the aqueous solution obtained by step (B) to separate into two layers of an organic layer and an aqueous layer, and then separating the oil layer and the aqueous layer thus obtained from each other. From the resulting oil layer are obtained 2-hydroxy-4-methylthiobutanoic acid of high quality and crystals of ammonium sulfate or crystals of sulfates including ammonium sulfate and ammonium bisulfate, in step (D), by adding ammonia (including aqueous ammonia) to the oil layer to neutralize at least part of the ammonium bisulfate in the oil layer to form ammonium sulfate, and then, through such operations as concentrating the oil layer, depositing and separating crystals of ammonium sulfate or crystals of sulfates including ammonium sulfate and ammonium bisulfate from the oil layer.

From the aqueous layer obtained by the layer separation, crystals including ammonium sulfate and ammonium bisulfate are deposited and separated, in step (E), by an appropriate crystallizing operation, e.g., concentration and/or cooling, and all or part of the aqueous solution containing ammonium sulfate and ammonium bisulfate thus obtained is recycled and used as the solution containing ammonium sulfate and ammonium bisulfate used in step (B).

In the present invention, in producing 2-hydroxy-4-methylthiobutanoic acid by subjecting 2-hydroxy-4-methylthiobutyronitrile to hydration and successive hydrolysis with sulfuric acid, an aqueous solution containing ammonium bisulfate and ammonium sulfate is added at the time of the hydrolysis reaction, to utilize a layer separation due to salting-out which takes place after the reaction.

In the present invention, in step (A) in which an aqueous solution of 2-hydroxy-4-methylthiobutyronitrile is contacted with sulfuric acid to effect hydration, it is preferable to add the aqueous 2-hydroxy-4-methylthiobutyronitrile solution by drops to sulfuric acid, whereby the hydration proceeds rapidly. The amount of sulfuric acid used is usually about 0.5 to about 1.0 mole, preferably about 0.6 to about 0.8 mole, relative to 1 mole of 2-hydroxy-4-methylthiobutyronitrile. When a 98% concentrated sulfuric acid is used, the water content of the aqueous solution of 2-hydroxy-4-methylthiobutyronitrile is preferably about 20–30% by weight. The sulfuric acid may also be used after preliminarily diluted with water. The reaction temperature is suitably about 40 to about 70° C. The reaction time is usually about 1–3 hours including the time used for dropwise addition, though it varies depending on the amount of sulfuric acid used.

In step (B), in which hydrolysis is conducted by adding an aqueous solution containing ammonium bisulfate and ammonium sulfate, the aqueous solution preferably contains an amount of water of about one time to about two times the weight of sulfuric acid used for the hydration of step (A). The addition of ammonium bisulfate exerts an effect of promoting the hydrolysis, and it is suitable to add the ammonium sulfate in an amount so as not to cause deposition of salts, namely ammonium sulfate, etc., in the aqueous solution to which the ammonium sulfate is added and so as not to cause deposition of such salts when the reaction system is still maintained at the high temperature subsequent to the hydrolysis reaction. Ammonium sulfate, the addition of which has an effect of greatly promoting spontaneous layer separation after the reaction, is used in the range of ammount of preferably about 0.1 to about 0.7 time, more preferably about 0.4 to about 0.6 time the weight of ammonium bisulfate, because too much addition of the salt slows down the progress of hydrolysis. When an aqueous solution containing ammonium sulfate in an amount exceeding about 0.7 time is added, the completion of reaction sometimes becomes later than in adding water containing no sulfates.

The amount of the aqueous solution containing ammonium bisulfate and ammonium sulfate used in step (B) is preferably such that the amount of ammonium sulfate in the aqueous solution might fall within the range of about 0.1 to about 0.4 mole relative to 1 mole of 2-hydroxy-4-methylthiobutyronitrile.

The aqueous solution containing ammonium bisulfate and ammonium sulfate used in step (B) may contain components other than ammonium bisulfate and ammonium sulfate, for example, organic substances such as 2-hydroxy-4-methylthiobutanoic acid, within the range which does not inhibit the hydrolysis or does not deteriorate the quality of the final product.

Though the temperature of the hydrolysis reaction is not particularly limited, it is preferably in the range of 90° C. to 130° C., because the higher the reaction temperature, the easier the progress of the reaction. Since the boiling point of the reaction liquid at atmospheric pressure in the present system is about 115° C., the reaction is preferably conducted in the neighborhood of the temperature. When a shorter reaction time is desired, the reaction may be conducted at a high temperature under an applied pressure by using a pressure-proof reaction apparatus.

Though the reaction time varies depending on the amounts of sulfuric acid and salts, such as ammonium sulfate, used, it is usually about 2 hours to 5 hours.

The hydrolysis is usually conducted while stirring. After the hydrolysis, when the stirring is stopped and the reaction liquid is allowed to stand, the liquid separates into two layers of an oil layer and an aqueous layer (step (C)). The layer separation proceeds the faster as the temperature is the higher; however, heating of the liquid is not always be needed since the layer separation is an operation succeeding to the hydrolysis reaction, which is usually conducted at a high temperature. Depending on the amounts of salts, ammonium bisulfate and ammonium sulfate, used in step (B), the deposition of the salts possibly occurs with the lowering of temperature of the reaction liquid and, therefore, sometimes the liquid may preferably be kept warm. The velocity of layer separation depends greatly on the amount of ammonium sulfate, etc. and the water content of the system. The most simple and useful method for promoting the progress of layer separation is to concentrate the liquid.

The compositions of the oil layer and the aqueous layer are affected by the amounts of ammonium bisulfate and ammonium sulfate, particularly the amount of ammonium sulfate, used at the time of hydrolysis. The higher the content of ammonium sulfate in the system, the more 2-hydroxy-4-methylthiobutanoic acid tends to be distributed to the oil layer side and the more sulfates tends to be distributed to the aqueous layer side.

To the oil layer after layer separation is added ammonia to neutralize at least part of ammonium bisulfate remaining in the oil layer into ammonium sulfate (step (D)). The amount of ammonia to be added is preferably about 0.2 to about 3 times by mole relative to ammonium bisulfate remaining in the oil layer. A more preferable amount of ammonia to be added depends on the water content of the intended 2-hydroxy-4-methylthiobutanoic acid product. For example, when the product is to be obtained with a water content of about 4 to about 10% by weight, the amount of ammonia added is preferably about 1 to about 3 times by mole relative to ammonium bisulfate remaining in the oil layer; when a product with a water content of less than about 4% by weight, more specifically about 3.5% by weight or less, particularly about 2% by weight or less is to be obtained, the amount of ammonia added is preferably about 0.2 to about 1.4 times by mole relative to the remaining ammonium bisulfate.

The source of ammonia used may be any of the ammonia gas, liquid ammonia and aqueous ammonia solution, but when a concentrating operation is done after neutralization, the use of ammonia gas or liquid ammonia is recommendable.

From the slurry (ammonia-added layer) obtained after neutralization are separated, through such operations as filtration or the like, crystals of ammonium sulfate or crystals of sulfates including ammonium sulfate and ammonium bisulfate, whereby 2-hydroxy-4-methylthiobutanoic acid is obtained to form the objective product. When the separated crystals of ammonium sulfate and other salts contain an unnegligible amount of 2-hydroxy-4-methylthiobutanoic acid, the 2-hydroxy-4-methylthiobutanoic acid contained may be recovered by washing the crystals of the salts with an appropriate amount of water and then returning the washing filtrate to the step of neutralizing the oil layer, or by mixing the crystals of the salts into the aqueous layer obtained by layer separation after the hydrolysis.

Further, concentration may be done before the separating operation conducted through filtration, etc., whereby the amount of ammonium sulfate remaining in the obtained 2-hydroxy-4-methylthiobutanoic acid can be reduced. For example, when the slurry is concentrated until its water content reaches about 10% by weight or less relative to the liquid portion in the slurry, and thereafter subjected to separating operation, such as filtration, the content of ammonium sulfate in the ultimate product, calculated in terms of sulfate ion ($SO_4^{2-}$ ion), can be reduced to 1% by weight or less without conducting any further operation. When a shorter filtration time is desired, it is most effective to raise the temperature of the slurry.

When the amount of ammonia added to the oil layer and the water content of the slurry before the separating operation are appropriately controlled, 2-hydroxy-4-methylthiobutanoic acid of higher quality can be obtained. For example, a 2-hydroxy-4-methylthiobutanoic acid product can be obtained which has a sulfate ion concentration in the product (determined after incorporating water thereinto so as to give a content of 2-hydroxy-4-methylthiobutanoic acid therein, measured by potentiometric titration, of about 89% by weight) of not higher than 1% by weight, has a kinematic viscosity of not higher than 90 cSt and hence is excellent in ease of handling.

When the amount of ammonia used for neutralization is too small, the concentration of sulfate ions contained in the product tends to be too high; on the other hand, when ammonia is added in excess, the kinematic viscosity of the product is sometimes too high. When the water content of the slurry before the separating operation is high, both the sulfate ion concentration in the product and the kinematic viscosity tend to be high. Therefore, when it is desired to obtain a product having both a low kinematic viscosity and a low sulfate ion concentration, it is advisable to conduct neutralization with an appropriate, small amount of ammonia and thereafter to distill off much of water from the slurry in the concentrating operation.

For example, a specific 2-hydroxy-4-methylthiobutanoic acid product can be obtained when ammonia is added to the oil layer in an amount of about 0.2 to about 1.4 molar equivalents relative to the ammonium bisulfate contained in the oil layer obtained after layer separation, then the slurry is concentrated until the water content of the slurry reaches 3.5% by weight or less relative to the liquid portion in the slurry, and thereafter the slurry is subjected to a separating operation without conducting any additional operation. The product has a sulfate ion ($SO_4^{2-}$ ion) concentration therein of not higher than about 1% by weight and a kinematic viscosity of not higher than about 90 cSt (as determined after incorporating water thereinto so as to give a content of 2-hydroxy-4-methylthiobutanoic acid therein, measured by polentiometric titration, of about 89% by weight).

In order that the neutralization be controlled in a simple and easy way, it may be controlled by using a pH value. In such a case, 2-hydroxy-4-methylthiobutanoic acid with the above-mentioned high quality can be obtained by adding ammonia so as to give a pH of the oil layer at 25° C. in the range of about 0.4 to about 2. The operation of neutralization may also be conducted at high temperatures, and the control may be conducted with a pH value measured at high temperatures.

Further, another specific 2-hydroxy-4-methylthiobutanoic acid product can be obtained, when ammonia is added to the slurry in an amount of about 0.2 to about 1.4 molar equivalents relative to ammonium bisulfate contained in the oil layer obtained after layer separation (or ammonia is added until the pH of the oil layer at 25° C. becomes between about 0.4 and about 2), then the slurry is concentrated until the water content thereof reaches about 2% by weight or less relative to the liquid portion in the slurry and thereafter the slurry is subjected to a separating operation, without conducting any additional operation. The product has a sulfate ion concentration therein of not higher than about 1% by weight and a kinematic viscosity of not higher than 80 cSt (as determined after incorporating water thereinto so as to give a content of 2-hydroxy-4-methylthiobutanoic acid therein, measured by potentiometric titration, of about 89% by weight).

In the present invention, by concentrating and/or cooling the aqueous layer obtained by layer separation and then conducting such operations as filtration, etc., salts comprising ammonium bisulfate and ammonium sulfate are separated as deposits and an aqueous solution containing ammonium bisulfate and ammonium sulfate is obtained (step (E)). The aqueous solution obtained above further contains 2-hydroxy-4-methylthiobutanoic acid. A part or the whole of the solution, as it is or after its water content has been adjusted, is utilized as the aqueous solution added in the hydrolysis reaction in step (B) (step (F)). The ratio of ammonium bisulfate to ammonium sulfate in the aqueous solution can be varied by controlling the crystallization conditions of concentration and/or cooling in obtaining the above-mentioned deposits of salts of ammonium sulfate, etc. The optimum conditions for the crystallization depend greatly on the composition of the salts of ammonium sulfate, etc. in the aqueous layer. Therefore, when the salts are deposited by cooling for example, it is advisable to determine appropriate crystallization conditions by preliminarily preparing the solubility curves of ammonium sulfate and ammonium bisulfate in the aqueous layer actually obtained, and then assuming a cooling temperature and estimating the salt composition of the filtrate obtained at the temperature.

Since the crystals of the salts thus obtained comprise a mixture of ammonium bisulfate and ammonium sulfate, when it is desired to recover them as ammonium sulfate, the recovery is preferably effected by neutralizing them with ammonia. The ammonia used may be in any of the forms of ammonia gas, liquid ammonia and aqueous ammonia solution. When the crystals contain a small amount of 2-hydroxy-4-methylthiobutanoic acid, it is preferable to contact an aqueous ammonia solution with the crystals to serve both for neutralization and washing and then to subject the resulting product to separating operations such as filtration, etc., whereby 2-hydroxy-4-methylthiobutanoic acid is recovered on the liquid side.

Such a neutralizing operation with ammonia may also be conducted after combining the above-mentioned salt crystals with the ammonium sulfate and other salts which have developed in other steps, for example, ammonium sulfate, etc. separated from the slurry obtained after neutralization of the oil layer. In such a way, salts of ammonium sulfate, etc. developed in plural spots can be handled together.

The ammonium sulfate obtained through such a neutralizing operation contains a small amount of 2-hydroxy-4-methylthiobutanoic acid. When an aqueous solution of the ammonium sulfate is contacted with active carbon and then subjected to such operations as crystallization, etc., a high quality, crystalline ammonium sulfate can be obtained as a by-product. In the case, 2-hydroxy-4-methylthiobutanoic acid is adsorbed to the active carbon; this not only prevents the accumulation of 2-hydroxy-4-methylthiobutanoic acid in the ammonium sulfate recovery system but also permits the removal of odor components, such as sulfides. It is needless to say that similar effects can also be expected when active carbon is contacted with the salts before neutralization with ammonia, namely in the state of a mixed aqueous solution of ammonium sulfate and ammonium bisulfate.

One embodiment of the present invention is described below with reference to a flow sheet (FIG. 1) shown in the form of block diagram.

First, concentrated sulfuric acid is placed in a reaction vessel and 2-hydroxy-4-methylthiobutyronitrile is added by drops thereto. After completion of the dropwise addition, the resulting mixture is held for 1–2 hours to effect hydration. The liquid temperature during the time is 40–70° C. Then, an aqueous solution containing ammonium bisulfate and ammonium sulfate obtained by the method described below is added, the resulting mixture is heated to 115° C. and held for 2–5 hours to effect a hydrolysis reaction.

Then the reaction liquid is allowed to stand and to separate into two layers, and the oil layer and the aqueous layer thus formed are separated from each other.

To the oil layer is added ammonia to neutralize ammonium bisulfate dissolving in the layer into ammonium sulfate, to obtain a slurry. Then the slurry is concentrated until the water content of the slurry reaches 10% by weight or less, preferably 3% by weight or less, more preferably 2% by weight or less, and then ammonium sulfate is removed by filtration, leaving behind a filtrate containing 2-hydroxy-4-methylthiobutanoic acid product.

The aqueous layer is subjected to a crystallizing operation by cooling and/or concentration and then filtered to separate the deposited ammonium bisulfate and ammonium sulfate, leaving behind an aqueous solution containing ammonium sulfate, ammonium bisulfate and 2-hydroxy-4-methylthiobutanoic acid as a filtrate. The aqueous solution is, after its water content has been adjusted, recycled and used as the aqueous solution to be added at the time of hydrolysis.

The deposited salt obtained in the above-mentioned filtration contains ammonium bisulfate. Therefore, when effective utilization thereof as ammonium sulfate is desired, it is neutralized with ammonia to recover the whole as ammonium sulfate. Further, the deposited salt contains some 2-hydroxy-4-methylthiobutanoic acid adhereing thereto. The acid can be recovered by washing the salt with water after neutralization with ammonia or by washing the salt with an aqueous ammonia solution, which serves both for neutralization and washing.

As set forth above, according to the process of the present invention, in producing 2-hydroxy-4-methylthiobutanoic acid, (1) addition of an aqueous solution containing ammonium bisulfate and ammonium sulfate to the step of hydrolysis of 2-hydroxy-4-methylthiobutanamide promotes the layer separation of the reaction liquid containing 2-hydroxy-4-methylthiobutanoic acid formed by hydrolysis into two layers, an oil layer and an aqueous layer, whereby a high quality 2-hydroxy-4-methylthiobutanoic acid can be separated without requiring organic solvents, and (2) the aqueous layer obtained by the layer separation can be recycled, after a simple operation, to the reaction system as an aqueous solution of ammonium bisulfate and ammonium sulfate.

Accordingly, the present invention makes it possible to constitute a process which requires no organic solvent and imposes very little waste water load. Thus, the invention is of great industrial value not only in the reduction of production cost but also from its environmental friendliness.

EXAMPLES

The process of the present invention is described in detail below with reference to Examples, but it is not limited thereto.

Example 1

To 196.8 g (1.4 moles) of a 70% aqueous sulfuric acid solution was added by drops, while stirring, 294.1 g (2.0 moles) of an 89.2% aqueous 2-hydroxy-4-methylthiobutyronitrile solution over 30 minutes. The inner temperature of the reaction mixture during the above dropwise addition was controlled so as to be about 50° C. After completion of the dropwise addition, the resulting mixture was stirred for further two hours while the inner temperature being kept at 50° C., to effect hydration.

To the resulting mixture were then added each of (a) 228.7 g of water, (b) a solution of 94.0 g of ammonium bisulfate dissolved in 228.7 g of water, (c) a solution of 94.0 g ammonium bisulfate and 39.6 g of ammonium sulfate dissolved in 228.7 g of water, (d) a solution of 94.0 of ammonium bisulfate and 52.8 g of ammonium sulfate dissolved in 228.7 g of water, and (e) a solution of 94.0 g of ammonium bisulfate and 79.3 g of ammonium sulfate dissolved in 228.7 g of water. The resulting mixtures were held at 115° C. while stirring, to effect hydrolysis. The changes in the hydrolysis with the lapse of time (elapsed from the addition of the solutions described in (a) to (e) above) are shown in Table 1 in terms of conversion to 2-hydroxy-4-methylthiobutanoamide. The analysis was made by liquid chromatography.

TABLE 1

| Solution used for hydrolysis | 1 hr | 2 hr | 3 hr | 4 hr | 5 hr |
|---|---|---|---|---|---|
| (a) | 97.16% | 99.24% | 99.79% | 99.89% | 99.93% |
| (b) | 99.16% | 99.91% | 99.97% | 100% | 100% |
| (c) | 99.57% | — | 99.88% | — | 99.98% |
| (d) | — | — | 99.83% | — | 99.94% |
| (e) | 93.92% | 98.36% | 99.52% | 99.76% | 99.93% |

Example 2

Each of the mixtures after the hydrolysis effected by the addition of (a) to (e) of Example 1 was allowed to stand and to separate into two layers. Then the mixtures were kept at 70° C. and allowed to stand to respectively separate an oil layer and an aqueous layer from each other. Then the respective layers were analyzed for their respective contents of 2-hydroxy-4-methylthiobutanoic acid (abbreviated as HMBA in Tables), ammonium bisulfate and ammonium sulfate. The results obtained are shown in Table 2 for the oil layer and in Table 3 for the aqueous layer.

The component analysis of the oil layer and the aqueous layer was conducted by liquid chromatography for 2-hydroxy-4-methylthiobutanoic acid and by ion chromatography for ammonium bisulfate and ammonium sulfate. The units are all in mole.

TABLE 2

Components of oil layer

| Solution used for hydrolysis | HMBA | Ammonium bisulfate | Ammonium sulfate |
|---|---|---|---|
| (a) | \multicolumn{3}{c}{No oil-water separation} | | |
| (b) | 1.714 | 0.532 | 0.244 |
| (c) | 1.790 | 0.335 | 0.168 |
| (d) | 1.850 | 0.277 | 0.189 |
| (e) | 1.868 | 0.202 | 0.193 |

TABLE 3

Components of aqueous layer

| Solution used for hydrolysis | HMBA | Ammonium bisulfate | Ammonium sulfate |
|---|---|---|---|
| (a) | \multicolumn{3}{c}{No oil-water separation} | | |
| (b) | 0.246 | 1.049 | 0.372 |
| (c) | 0.159 | 1.235 | 0.738 |
| (d) | 0.141 | 1.214 | 0.863 |
| (e) | 0.121 | 1.256 | 1.082 |

Example 3

The ammonium bisulfate in the oil layer (456.1 g) obtained in (c) of Example 2 was neutralized with a sufficient amount of an 25% aqueous ammonia solution (45 g). The resulting liquid was divided into 6 portions. Each portion was concentrated to the concentrating rate shown in Table 4, then cooled to room temperature and filtered to obtain 2-hydroxy-4-methylthiobutanoic acid product as the filtrate. The water content and the sulfate ion concentration in the product obtained at each concentration rate are shown in Table 4.

The sulfate ion concentration was determined by using ion chromatography and the water content by using a moisture meter by Karl Fischer's method.

TABLE 4

| Concentration rate | 100% (Not concentrated) | 86% | 84% | 82% | 80% | 76% |
|---|---|---|---|---|---|---|
| Water content | 24.5% | 14.0% | 12.7% | 10.4% | 8.5% | 3.3% |
| Sulfate ion | 6.2% | 1.8% | 1.4% | 0.95% | 0.62% | 0.23% |

Example 4

The following operations ①–④ were conducted.

① To 96.6 g (0.7 mole) of 71% sulfuric acid was added by drops 148 g (1.0 mole) of an 88.7% aqueous 2-hydroxy-4-methylthiobutyronitrile solution over 30 minutes while stirring and the resulting mixture was thereafter held while stirring for 90 minutes.

② An aqueous sulfate solution was prepared by using 70 g (0.6 mole) of ammonium bisulfate, 33 g (0.25 mole) of ammonium sulfate and 114 g of water. The solution was added to the reaction mixture obtained in ① above, and the resulting mixture was allowed to react at 115° C. for 4 hours. The mixture after the reaction was allowed to stand and to separate into two layers (an oil layer and an aqueous layer), and the layers were separated from each other.

③ To the oil layer obtained in ② above was added 13.6 g (0.2 mole) of a 25% aqueous ammonia solution, and the resulting mixture was concentrated until the water content of the oil layer reached 10% or less relative to the liquid portion in the mixture. Thereafter, by filtration, 2-hydroxy-4-methylthiobutanoic acid product was obtained in the filtrate and ammonium sulfate in the cake.

④ The aqueous layer obtained in ② above was cooled to 30° C., and the deposited ammonium sulfate was separated by filtration. About 5 to about 10% of the filtrate was discharged out of the system so that the composition and the amount of sulfates in the filtrate might be constant. Then water was added to the remaining filtrate so that the amount of water in the filtrate might become 114 g, thereby to prepare an aqueous sulfate solution.

In the same manner as described above except for using the aqueous sulfate solution prepared in ④ above in place of the aqueous solution prepared in ② by using ammonium bisulfate and ammonium sulfate, the operations of ① to ④ described above were repeated 3 times.

Table 5 shows the content of 2-hydroxy-4-methylthiobutanoic acid (including its dimer; unit:mole) 5 in the oil layer and aqueous layer, the content being determined for each of the above-mentioned 4 times-repeated experiments. The analysis was made by liquid chromatography.

TABLE 5

| Number of time of experiment | In oil layer | In aqueous layer |
|---|---|---|
| 1st time | 0.926 | 0.073 |
| 2nd time | 0.945 | 0.078 |
| 3rd time | 0.968 | 0.070 |
| 4th time | 0.943 | 0.072 |

Table 6 shows the ratio of ammonium bisulfate (mole) to ammonium sulfate (mole) in the aqueous sulfate solution added in ②, the ratio of ammonium bisulfate (mole) to ammonium sulfate (mole) in the aqueous layer obtained in ②, and the ratio of ammonium bisulfate (mole) to ammonium sulfate (mole) in the sulfates crystals separated from the aqueous layer in ④. The analysis was made by a combination of neutralization titration using NaOH and ion chromatography.

TABLE 6

|  | Composition * of aqueous layer obtained in ② | Aqueous layer | Composition * of sulfates obtained in ④ |
| --- | --- | --- | --- |
| 1st time | 0.600/0.250 | — | 0.205/0.186 |
| 2nd time | 0.605/0.269 | 0.879/0.500 | 0.198/0.186 |
| 3rd time | 0.608/0.270 | 0.862/0.506 | 0.228/0.200 |
| 4th time | 0.606/0.267 | 0.902/0.514 | 0.205/0.187 |

Note:
*: molar ratio of ammonium bisulfate/ammonium sulfate

The results shown in Tables 5 and 6 reveal that the compositions of the oil layer and the aqueous layer obtained after the reaction and the compositions of the aqueous sulfate solution and the sulfate crystals separated from the aqueous layer by crystallization are constant and steady through the experiments.

Table 7 shows the composition of the product obtained in the experiments repeated 4 times. 2-Hydroxy-4-methylthiobutanoic acid and its dimer were analyzed by liquid chromatography, the sulfate ion by ion chromatography, and the water content by a moisture meter by Karl Fischer's method. The color was expressed by the Gardner color scale.

TABLE 7

|  | HMBA | HMBA dimer | Sulfate ion | Water content | Color |
| --- | --- | --- | --- | --- | --- |
| 1st time | 76.19% | 15.26% | 0.38% | 6% | 13 |
| 2nd time | 75.54% | 14.66% | 0.62% | 7% | 13 |
| 3rd time | 74.58% | 15.08% | 0.59% | 8% | 13 |
| 4th time | 68.77% | 13.55% | 1.65% | 14% | 13 |

The results obtained above show that products with approximately constant composition were obtained, although the sulfate ion content in the product was high only in the 4th time operation because the concentration in operation ③ was insufficient at that time.

Example 5

The following operations ①–⑧ were conducted as the experiment of the first time.

① To 197.9 g (1.4 moles) of a 69.3% aqueous sulfuric acid solution was added by drops, while stirring, 293 g (2.0 moles) of an 89.6% aqueous 2-hydroxy-4-methylthiobutyronitrile solution over 30 minutes, and the resulting mixture was held while stirring for further 90 minutes.

② An aqueous sulfate solution was prepared by using 140 g (1.2 moles) of ammonium bisulfate, 66 g (0.5 mole) of ammonium sulfate and 228 g of water. The solution was added to the reaction mixture obtained in ① above, and the resulting mixture was allowed to react at 115° C. for 4 hours. The mixture after the reaction was allowed to stand and to separate into two layers, and the layers were separated from each other.

③ To the oil layer thus obtained were added the washing filtrate obtained in ④ (which, however, was not used in the first time of experiment) and 20 g of a 25% aqueous ammonia solution, and the resulting mixture was concentrated under reduced pressure until the water content of the oil layer reached 10% or less relative to the liquid portion in the oil layer. Thereafter, by filtration, the objective product was obtained in the filtrate and ammonium sulfate crystals in the deposit.

④ The ammonium sulfate obtained in ③ was washed with 30 g of water and filtered to obtain ammonium sulfate and a washing filtrate.

⑤ The aqueous layer was cooled to 25° C. and then the deposited ammonium sulfate was separated by filtration. Then, from 0 to about 10% of the filtrate was discharged out of the system so that the composition and the amount of the sulfates in the filtrate might be constant. Then, water was added to the remaining filtrate so that the amount of water in the filtrate might become 228 g, thereby the prepare an aqueous sulfate solution.

⑥ Parts of the ammonium sulfate and the filtrate formed in ④ and ⑤ were dissolved in 300–400 g of water. To this solution were added the filtrate obtained in ⑧ (which, however, was not used in the first time of experiment) and 30–40 g of a 25% aqueous ammonia solution, to obtain an aqueous ammonium sulfate solution.

⑦ To the aqueous ammonium sulfate solution obtained in ⑥ was added 6–7 g (corresponding to 1% by weight of the aqueous solution) of active carbon. The resulting mixture was stirred at room temperature for one hour and then filtered.

⑧ The filtrate obtained in ⑦ was concentrated under reduced pressure until a concentration rate of 40% was reached, and then filtered at room temperature to obtain ammonium sulfate crystals.

In the same manner as described above except for using the aqueous sulfate solution prepared in ⑤ in place of the aqueous solution prepared in ② by using ammonium bisulfate and ammonium sulfate, the operations of ①–⑪ described above were repeated 5 times.

Table 8 shows the amount of the product obtained, the yield, and the content of 2-hydroxy-4-methylthiobutanoic acid (including the dimer, unit: mole) in the operation ③ of each experiment in the above-mentioned experiments repeated 6 times. The analysis was made by liquid chromatography.

TABLE 8

|  | Amount obtained | HMBA content | Yield |
| --- | --- | --- | --- |
| 1st time | 237.2 g | 98.6% | 79.0% |
| 2nd time | 323.5 g | 92.8% | 99.9% |
| 3rd time | 304.7 g | 93.5% | 94.9% |
| 4th time | 292.8 g | 92.3% | 90.0% |
| 5th time | 328.1 g | 90.6% | 99.0% |
| 6th time | 312.3 g | 97.5% | 101.4% |

In Table 8, the yields at the first time and the fourth time are low. As for the first time, this is because 2-hydroxy-4-methylthiobutanoic acid adhering to the sulfate crystals obtained in the filtration conducted after concentration of the oil layer was carried over on and after the second time. As for the fourth time, this is because the filtration time was set shorter than in other times of experiment and hence more 2-hydroxy-4-methylthiobutanoic acid was adhered to the sulfate crystals. Anyhow, since almost all of the adhering HMBA is recovered on and after the next time, the average yield on and after the second time of experiment is as high as 97% or more.

Table 9 shows the amount of the washing filtrate obtained in ④ and the content of 2-hydroxy-4-methylthiobutanoic acid (including the dimer; mole) in the washing filtrate, in the above-mentioned experiments repeated 6 times.

TABLE 9

|  | Amount of washing filtrate | HMBA |
|---|---|---|
| 1st time | 142.2 g | 0.21 mole |
| 2nd time | 145.9 g | 0.15 mole |
| 3rd time | 120.2 g | 0.18 mole |
| 4th time | 158.0 g | 0.36 mole |
| 5th time | 187.4 g | 0.27 mole |
| 6th time | 186.9 g | 0.24 mole |

Table 10 shows the composition (in mole) of the aqueous sulfate solution prepared in ⑤ (the solution used in ② of the next experiment), in the above-mentioned experiments repeated 6 times. The respective sulfates were analyzed by ion chromatography.

TABLE 10

|  | Ammonium bisulfate | Ammonium sulfate | HMBA |
|---|---|---|---|
| 1st time | 1.200 moles | 0.500 mole | — |
| 2nd time | 1.316 moles | 0.549 mole | 0.14 mole |
| 3rd time | 1.221 moles | 0.581 mole | 0.09 mole |
| 4th time | 1.188 moles | 0.500 mole | 0.09 mole |
| 5th time | 1.277 moles | 0.590 mole | 0.10 mole |
| 6th time | 1.190 moles | 0.419 mole | 0.10 mole |

Table 11 shows the content of 2-hydroxy-4-methylthiobutanoic acid (including the dimer; mole) in the aqueous ammonium sulfate solution obtained in ⑥ and the amount of 2-hydroxy-4-methylthiobutanoic acid (including the dimer; mole) contained in the solution obtained after the active carbon treatment of ⑦, in the above-mentioned experiments repeated 6 times.

TABLE 11

|  | Aqueous solution obtained in ⑥ (Before active carbon treatment) | Aqueous solution obtained in ⑦ (After active carbon treatment) |
|---|---|---|
| 1st time | 0.026 mole | 0.008 mole |
| 2nd time | 0.016 mole | 0.006 mole |
| 3rd time | 0.018 mole | 0.006 mole |
| 4th time | 0.010 mole | 0.004 mole |
| 5th time | 0.048 mole | 0.014 mole |
| 6th time | 0.018 mole | 0.006 mole |

Table 11

Table 12 shows the concentration of the odor components (dimethyl sulfide, dimethyl disulfide) in the ammonium sulfate crystals obtained in ⑧, in the above-mentioned experiments repeated 6 times. The odor components were analyzed by head space gas chromatography.

TABLE 12

|  | Dimethyl sulfide | Dimethyl disulfide |
|---|---|---|
| 1st time | 0.04 ppm | 0.02 ppm |
| 2nd time | 0.04 ppm | ≧0.01 ppm |

TABLE 12-continued

|  | Dimethyl sulfide | Dimethyl disulfide |
|---|---|---|
| 3rd time | ≧0.01 ppm | ≧0.01 ppm |
| 4th time | ≧0.01 ppm | 0.03 ppm |
| 5th time | 0.08 ppm | 0.04 ppm |
| 6th time | Not determined | Not determined |
| No active carbon treatment | 0.20 ppm | 0.10 ppm |

Example 6

The same operations as ① and ② of Example 4 were conducted to obtain an oil layer, which was then neutralized with 0–8.6 g of a 25% aqueous ammonia solution (corresponding to 0–1.2 molar equivalents relative to the ammonium bisulfate used in ⑧), and water was distilled off with an evaporator. The resulting slurry was filtered at 70° C., and the filtrate was measured for its water content and the content of 2-hydroxy-4-methylthiobutanoic acid.

Then, water was added to the filtrate so that the content of 2-hydroxy-4-methylthiobutanoic acid therein might become 89.0% by weight, thereby to prepare the product.

The content of 2-hydroxy-4-methylthiobutanoic acid was determined by potentiometric titration, the water content by the Karl Fischer's method, the sulfate ion by ion chromatography and the kinematic viscosity by a Cannon-Fenske viscometer at 25° C.

Table 13 shows the amount of ammonia, the pH of the oil layer at 25° C., the water content (% by weight) of the filtrate, the sulfate ion concentration (% by weight) in the product and the kinematic viscosity (cSt) thus determined.

TABLE 13

| Ammonia amount* | Oil layer pH (25° C.) | Water content of filtrate (wt %) | Sulfate ion concentration (wt %) | Kinematic viscosity (cSt) |
|---|---|---|---|---|
| 0 | 0.2 | 0.63 | 2.04 | — |
| 0 | 0.2 | 1.63 | 2.32 | — |
| 0.1 | 0.36 | 0.57 | 0.91 | — |
| 0.1 | 0.36 | 1.85 | 1.17 | — |
| 0.1 | 0.36 | 2.60 | 1.43 | — |
| 0.2 | 0.41 | 0.90 | 0.52 | 66.5 |
| 0.2 | 0.41 | 2.30 | 0.76 | 74.3 |
| 0.2 | 0.41 | 2.90 | 0.86 | 80.0 |
| 0.3 | 0.59 | 0.70 | 0.43 | 73.5 |
| 0.3 | 0.59 | 1.70 | 0.58 | 77.1 |
| 0.3 | 0.59 | 2.50 | 0.69 | 78.1 |
| 0.4 | 0.65 | 1.20 | 0.61 | 73.3 |
| 0.4 | 0.65 | 2.20 | 0.75 | 78.6 |
| 0.4 | 0.65 | 3.10 | 0.97 | 80.5 |
| 0.7 | 0.88 | 1.10 | 0.60 | 73.8 |
| 0.7 | 0.88 | 1.99 | 0.73 | 78.3 |
| 0.7 | 0.88 | 2.91 | 0.87 | 81.9 |
| 0.7 | 0.88 | 3.88 | 1.09 | 84.8 |
| 0.8 | 0.99 | 0.90 | 0.54 | 74.7 |
| 0.8 | 0.99 | 1.94 | 0.71 | 78.6 |
| 0.8 | 0.99 | 3.08 | 0.85 | 79.1 |
| 0.8 | 0.99 | 3.92 | 1.04 | 80.0 |
| 0.9 | 1.10 | 0.80 | 0.53 | 72.8 |
| 0.9 | 1.10 | 2.03 | 0.70 | 80.3 |
| 0.9 | 1.10 | 2.64 | 0.80 | 79.1 |
| 0.9 | 1.10 | 3.58 | 1.02 | 88.9 |
| 1.0 | 1.27 | 1.00 | 0.54 | 70.9 |
| 1.0 | 1.27 | 2.09 | 0.70 | 74.5 |
| 1.0 | 1.27 | 2.85 | 0.85 | 78.6 |
| 1.0 | 1.27 | 3.72 | 0.99 | 84.4 |
| 1.0 | 1.27 | 4.67 | 1.31 | — |
| 1.1 | 1.53 | 0.66 | 0.57 | 69.4 |

TABLE 13-continued

| Ammonia amount* | Oil layer pH (25° C.) | Water content of filtrate (wt %) | Sulfate ion concentration (wt %) | Kinematic viscosity (cSt) |
|---|---|---|---|---|
| 1.1 | 1.53 | 1.66 | 0.73 | 74.0 |
| 1.1 | 1.53 | 2.86 | 0.89 | 80.7 |
| 1.2 | 1.73 | 0.81 | 0.40 | 69.7 |
| 1.2 | 1.73 | 1.99 | 0.55 | 76.2 |
| 1.2 | 1.73 | 3.34 | 0.65 | 78.6 |

Note:
*Unit is molar equivalent relative to ammonium bisulfate in oil layer
—: Not determined

What is claimed is:

1. A process for producing 2-hydroxy-4-methylthiobutanoic acid comprising the steps of:
   (A) contacting an aqueous solution of 2-hydroxy-4-methylthiobutyronitrile with sulfuric acid to obtain an aqueous solution containing 2-hydroxy-4-methylthiobutanamide,
   (B) adding an aqueous solution containing ammonium bisulfate and ammonium sulfate to the solution obtained by step (A) to obtain an aqueous solution containing 2-hydroxy-4-methylthiobutanoic acid,
   (C) allowing the aqueous solution obtained by step (B) to separate into two layers of an oil layer and an aqueous layer, and then separating the oil layer and the aqueous layer from each other,
   (D) adding ammonia to the oil layer separated in step (C) to neutralize at least part of the ammonium bisulfate in the oil layer to form crystals of ammonium sulfate or crystals of sulfates including ammonium sulfate and ammonium bisulfate, and thereafter removing the crystals from the neutralized oil layer to obtain 2-hydroxy-4-methylthiobutanoic acid,
   (E) cooling and/or concentrating the aqueous layer separated in step (C) to obtain an aqueous solution containing ammonium bisulfate and ammonium sulfate as well as crystals of sulfates including ammonium sulfate and ammonium bisulfate, and
   (F) recycling all or part of the aqueous solution containing ammonium bisulfate and ammonium sulfate obtained by step (E), to step (B) as the aqueous solution containing ammonium bisulfate and ammonium sulfate.

2. The process according to claim 1, wherein in step (A) the sulfuric acid is used in an amount of from 0.6 to 0.8 molar equivalent relative to 2-hydroxy-4-methylthiobutyronitrile.

3. The process according to claim 1, wherein the aqueous solution containing ammonium bisulfate and ammonium sulfate in step (B) contains ammonium sulfate in an amount 0.1 to 0.7 times that of ammonium bisulfate in weight basis.

4. The process according to claim 1, wherein step (E) further includes the step of neutralizing the crystals of sulfates including ammonium sulfate and ammonium bisulfate with ammonia to recover the sulfates as ammonium sulfate.

5. The process according to claim 1, wherein step (D) further includes the step of washing the crystals of ammonium sulfate or the crystals of sulfates including ammonium sulfate and ammonium bisulfate with water and using all or part of the washings for the neutralization in step (D).

6. The process according to claim 1, which further comprises the step of:
   (G) dissolving all or part of the ammonium sulfate and/or the ammonium bisulfate obtained in any one, two or three of steps (D), (E) and (F) in water and neutralizing the resulting solution with ammonia to obtain an aqueous solution of ammonium sulfate.

7. The process according to claim 6, wherein step (G) further includes the step of contacting all or part of the aqueous solution of ammonium sulfate with active carbon.

8. The process according to claim 1, wherein in step (D) the ammonia is added to the oil layer in an amount of about 0.2 to about 3 molar equivalents relative to the ammonium bisulfate in the oil layer, and then the ammonia-added layer is concentrated until the layer contains 10% by weight or less of water relative to a liquid portion in the layer.

9. The process according to claim 1, wherein in step (D) the ammonia is added to the oil layer so that the resulting layer has a pH falling within the range of from 0.4 to 2.0 at 25° C., and then the ammonia-added layer is concentrated until the ammonia-added layer contains about 3.5% by weight or less of water relative to a liquid portion in the ammonia-added layer.

10. The process according to claim 9, wherein the ammonia-added layer is concentrated until the ammonia-added layer contains about 2% by weight or less of water relative to a liquid portion in the ammonia-added layer.

11. The process according to claim 1, wherein in step (D) the ammonia is added to the oil layer in an amount of from about 1 to about 3 molar equivalents relative to the ammonium bisulfate in the oil layer, and then the ammonia-added layer is concentrated until the ammonia-added layer contains about 4 to about 10% by weight of water relative to a liquid portion in the ammonia-added layer.

12. The process according to claim 1, wherein in step (D) the ammonia is added to the oil layer in an amount of from about 0.2 to about 1.4 molar equivalents relative to the ammonium bisulfate in the oil layer, and then the ammonia-added layer is concentrated until the ammonia-added layer contains about 3.5% by weight or less of water relative to a liquid portion in the ammonia-added layer.

13. The process according to claim 1, wherein in step (D) the ammonia is added to the oil layer in an amount of from 0.2 to 1.4 molar equivalents relative to the ammonium bisulfate in the oil layer, and then the ammonia-added layer is concentrated until the ammonia-added layer contains about 2% by weight or less of water relative to a liquid portion in the ammonia-added layer.

14. The process according to claim 1, wherein the removal of the crystals from the oil layer in step (D) is conducted at a temperature of about 40° C. or above.

* * * * *